United States Patent [19]
Chin et al.

[11] Patent Number: 5,415,182
[45] Date of Patent: May 16, 1995

[54] MULTIPLE NEEDLE BIOPSY INSTRUMENT

[75] Inventors: Yem Chin, Burlington; Michael S. H. Chu, Brookline, both of Mass.

[73] Assignee: Boston Scientific Corporation, Watertown, Mass.

[21] Appl. No.: 138,370

[22] Filed: Oct. 15, 1993

Related U.S. Application Data

[63] Continuation of Ser. No. 880,648, May 11, 1992, abandoned.

[51] Int. Cl.$^6$ ............................................. A61B 10/00
[52] U.S. Cl. ................................... 128/754; 128/749; 128/751; 606/167; 606/170
[58] Field of Search ............... 128/749, 751, 752, 753, 128/754, 755, 760, 763, 762, 770; 606/167, 168, 170, 171, 183, 185, 186, 188; 206/363, 364, 365, 366, 370, 375, 380, 443

[56] References Cited

U.S. PATENT DOCUMENTS

| | | |
|---|---|---|
| 3,086,530 | 4/1963 | Groom . |
| 3,512,518 | 5/1970 | Mishkin . |
| 4,476,864 | 10/1984 | Tezel ................... 128/754 |
| 4,620,547 | 11/1986 | Boebel ................. 128/754 |
| 4,907,599 | 3/1990 | Taylor .................. 128/754 |
| 4,958,625 | 9/1990 | Bates et al. ........... 128/754 |
| 4,976,269 | 12/1990 | Mehl .................... 128/754 |
| 5,012,818 | 5/1991 | Joishy .................. 128/754 |
| 5,195,533 | 3/1993 | Chin et al. ............ 128/754 |

FOREIGN PATENT DOCUMENTS

153047  8/1985  European Pat. Off. ............ 128/754

*Primary Examiner*—Peter A. Aschenbrenner
*Assistant Examiner*—Guy V. Tucker
*Attorney, Agent, or Firm*—Pearson & Pearson

[57] ABSTRACT

A biopsy needle instrument for capturing a plurality of discrete specimens. The instrument includes a housing, for supporting a plurality of axially elongated stylets and cannulas disposed about each stylet to form a plurality of biopsy needles. The cannula and stylet associated with each needle can be controlled independently or in conjunction with some other needles or all the needles. An elongated sheath supports the needles, can reposition the needles and control the specimen depth.

46 Claims, 9 Drawing Sheets

MULTIPLE NEEDLE BIOPSY INSTRUMENT

CROSS REFERENCE TO RELATED APPLICATION

This is a continuation of my patent application Ser. No. 07/880,648 filed May 11, 1992 for a Multiple Needle Biopsy Instrument, now abandoned.

BACKGROUND OF THE INVENTION

1. Field of the Invention

This invention generally relates to surgical biopsy instruments and more specifically to a method and apparatus for obtaining multiple biopsy specimens.

2. Description of Related Art

A biopsy needle instrument is frequently used to obtain a tissue specimen for microscopic examination to determine malignancy, While subjecting the patient to the least trauma. Typically, the instrument consists of a long, thin probe, termed a stylet, within a close-fitting hollow needle, termed a cannula. A firing device first projects the stylet into the tissue, followed immediately by the cannula. The stylet has a notch into which tissue will prolapse when the stylet enters the tissue. As the cannula subsequently slides over the stylet, it severs the prolapsed tissue from the surrounding mass and captures the prolapsed tissue as a specimen within the notch. The instrument then is typically withdrawn and the piece of tissue removed from the stylet.

U.S. Pat. No. 4,958,625 of Bates et al that issued Sep. 25, 1990 for a Biopsy Needle Instrument (assigned to the same assignee as the present invention) discloses a biopsy instrument needle that extends the stylet and the cannula when a firing button is pushed. A physician cocks a firing mechanism by retracting the cannula and the stylet individually into latched, spring-loaded positions. After orienting the distal end of the biopsy needle instrument, the physician activates the firing button. The stylet latch releases. As the stylet extends into the tissue, a portion of that tissue prolapses into a side-facing notch as a specimen. When the stylet reaches its extended position, it releases a cannula latch. The cannula slides over the stylet and severs the prolapsed tissue in the notch from any surrounding tissue and covers the notch thereby capturing the specimen. Next the physician removes the entire needle assembly from the patient and then extracts the biopsy specimen from the notch before another specimen can be taken.

In the foregoing patent, the cannula has a one-piece construction. As an alternative, the cannula can comprise two axially aligned tubular sections joined by a releasable fitting such as a Luer-lock fitting. In this configuration the distal cannula section constitutes a removable sheath that can be positioned independently of the remaining portions of the instrument. This is particularly useful for verifying instrument placement by various imaging means. Once the orientation is verified, the physician can reinsert the end of the stylet through the sheath and lock the two cannula sections together prior to taking a specimen. The removable sheath also facilitates the extraction of a specimen from the notch as its removal provides unobstructed access to the notch.

In many situations it is desirable to obtain plural tissue specimens either by repositioning or relocating the biopsy needle. Relocating the biopsy needle involves the withdrawal of the needle from the immediate tissue mass for insertion into adjacent tissue without withdrawing the needle from the patient. Repositioning the biopsy needle involves the complete withdrawal of the needle from the patient. When the foregoing biopsy instrument needle is used without a removable sheath, it is not possible merely to relocate the needle. If a removable sheath is used, relocation is possible. However, it is necessary to completely withdraw the needle from the sheath after each biopsy in order to extract and *identify each specimen. Consequently, prior art biopsy needle instruments effectively require repositioning for each biopsy even when the instrument includes a removable sheath. This repositioning process can be time consuming and it complicates biopsy procedures. Even if a two-piece cannula is used, the requirement for reattaching the needle instrument with its integral cannula section to the detached cannula section further complicates the biopsy procedures.

Application Ser. No. 881,028 filed May 8, 1992 and issued as U.S. Pat. No. 5,195,533 on Mar. 23, 1993, covers a biopsy needle instrument for storing multiple specimens. This biopsy needle instrument has a single stylet and cannula. An elongated notch formed in the stylet enables this single needle instrument to capture multiple specimens without repositioning. Thus this biopsy needle instrument enables a physician to obtain multiple specimens merely be relocating the biopsy needle. This eliminates any requirement for repositioning and can minimize patient trauma and this single needle instrument is particularly useful when access to a tissue site is restricted.

There are applications in which it can be helpful to a diagnosis to obtain a plurality of tissue samples from precisely located positions in a predetermined pattern. This precision involves both the location of each specimen site relative to the other sites in the pattern and the depth of each site. When a single needle instrument is utilized in these applications, the physician's dexterity can determine the precision of the pattern. Consequently, it can be difficult for a physician using a single needle instrument to obtain a precise pattern as the needle is relocated from one site to another and advanced into the tissue for some depth. Moreover, relocation of the needle instrument can increase patient trauma, complicate the biopsy process and increase the time required for obtaining the biopsies.

SUMMARY

Therefore it is an object of this invention to provide a biopsy needle instrument and biopsy method for capturing multiple tissue specimens.

Another object of this invention is to provide a biopsy needle instrument and biopsy method for capturing multiple specimens without the requirement for repositioning or relocating the instrument.

Still another object of this invention is to provide a biopsy needle instrument and biopsy method for capturing multiple specimens without the necessity for completely removing the biopsy needle from the patient.

Yet another object of this invention is to provide biopsy needle instrument and biopsy method that are adapted for obtaining specimens from a precise, predetermined pattern of tissue sites.

Still yet another object of this invention is to provide a biopsy needle instrument and biopsy method for capturing multiple specimens that is relatively easy to use in a variety of environments and is efficient.

In accordance with one aspect of this invention a biopsy needle instrument for taking multiple specimens from surrounding tissue in a predetermined pattern includes a housing, a plurality of axially elongated stylet means, a cannula means surrounding each stylet means and displacement means for moving the stylet means and the cannula means relative to each other and to the housing. Each stylet defines a specimen position according to a predetermined pattern. When the stylet means and cannula means are displaced distally, the biopsy needle instrument obtains multiple specimens from the tissue in the predetermined pattern.

In accordance with another aspect of this invention, multiple biopsies are obtained from a tissue mass in a predetermined pattern by first grouping a plurality of elongated stylets and coaxial cannulas along essentially parallel axes from proximal to distal ends in the predetermined pattern. Next the grouped stylets and cannulas are positioned proximate the tissue mass. Thereafter at least one of the stylets is displaced distally into the tissue thereupon causing corresponding cannulas to displace distally into the tissue to capture a specimen at each stylet. The displacement of all the stylets and cannula associated with the instrument capture plural specimens from the positions of the predetermined pattern.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
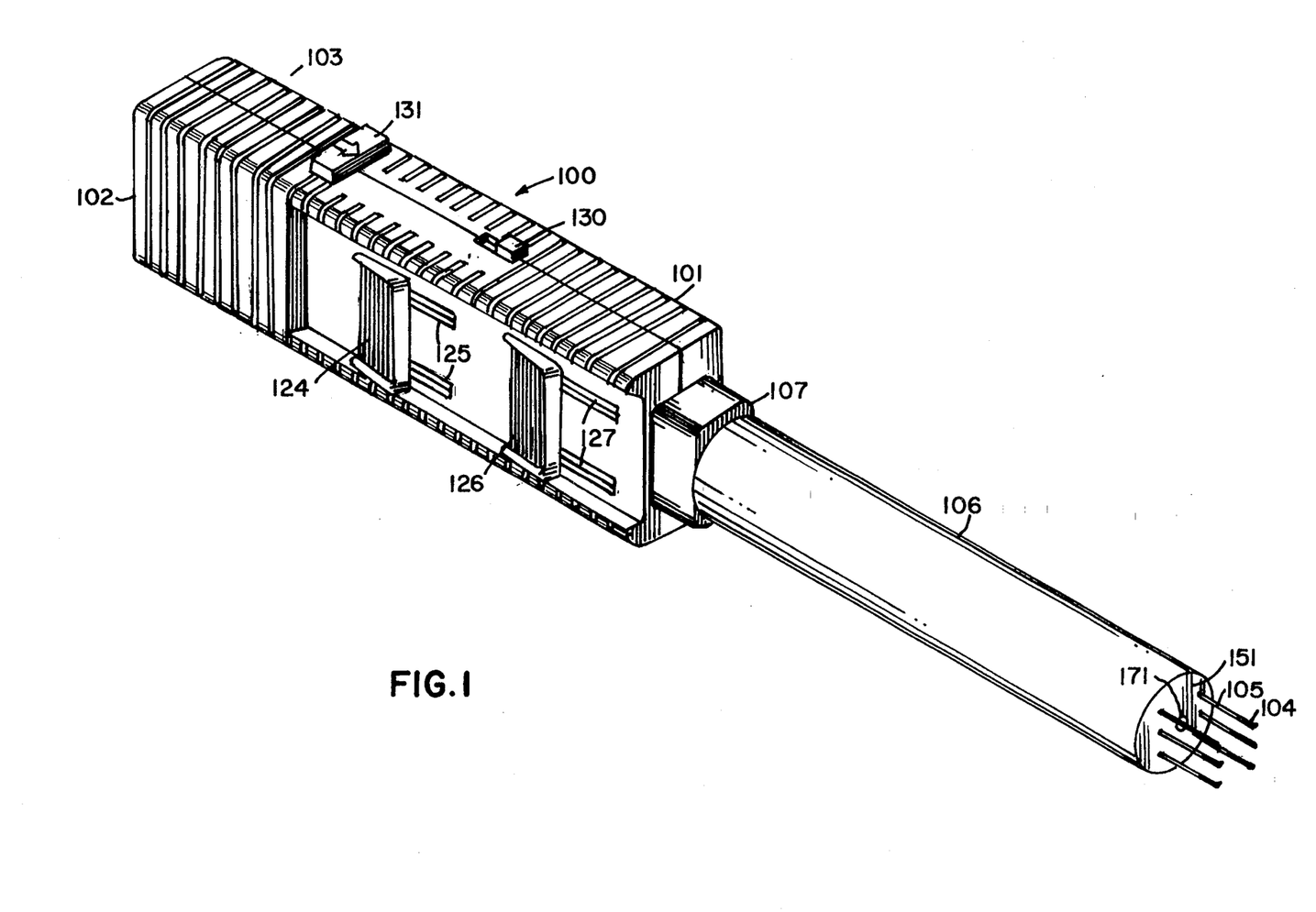
FIGS. 1 and 2 disclose one embodiment of a biopsy needle instrument that incorporates this invention.
Figure 2:
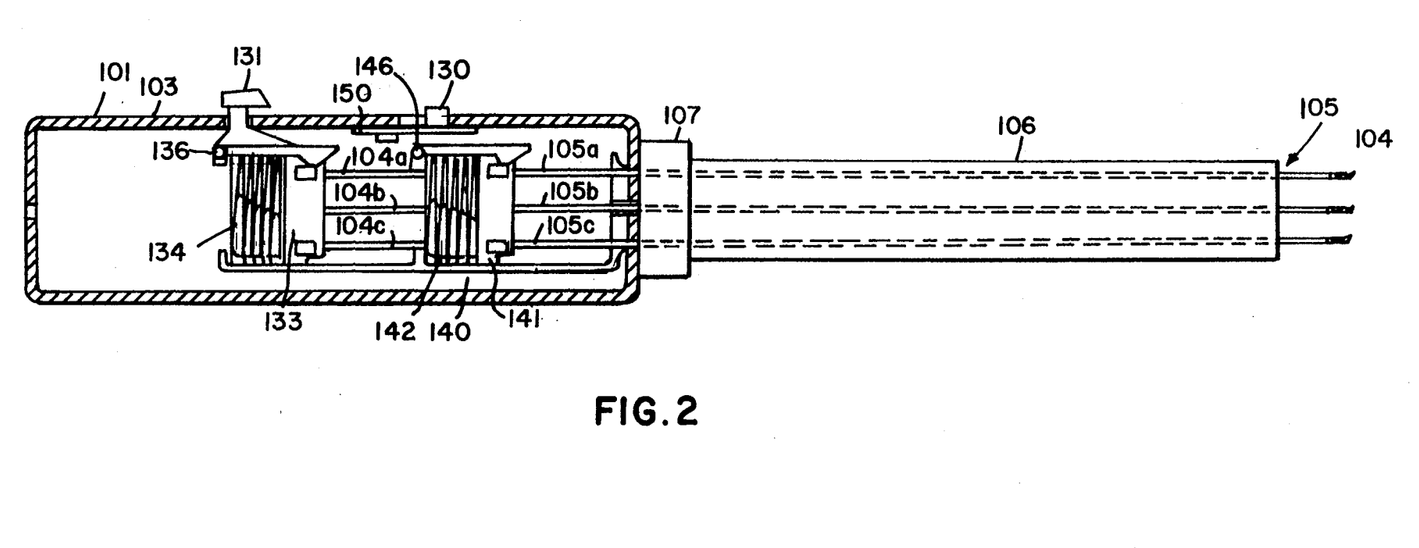

FIGS. 1 and 2 disclose a biopsy needle instrument 100 having a control housing 101 formed by a housing cover 102 and a housing base 103. This biopsy needle instrument 110 contains a plurality of stylets 104 and cannulas 105 that exit the distal end of a sheath 106 in a circular pattern. An end block 107 on the distal end of the control housing 101 supports the sheath 106.

Figure 3A:
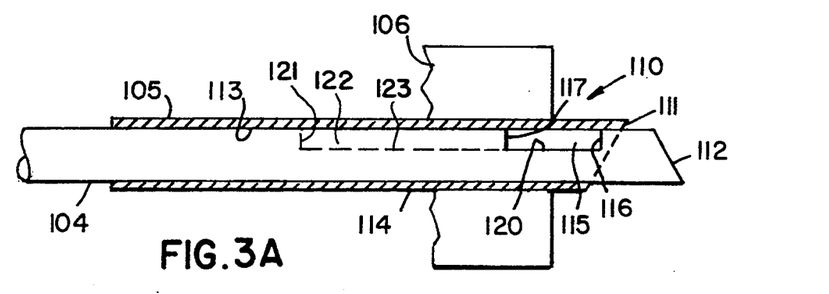
FIGS. 3A, 3B and 3C are enlarged views of portions of the biopsy needle instrument in FIG. 1.

FIG. 3A depicts, in cross-sectional view, the structure of a stylet 104 and a cannula 105 at a distal end 110 of the instrument. The cannula 105 terminates with a beveled cutting edge 111. The stylet 104 has an oppositely beveled distal end 112. The stylet 104 lies in a passage 113 formed by the cannula 105 and the stylet 104 and cannula 105 can move relative to each other. The cannula 105 additionally contains a marker 114 for facilitating the proper orientation of the instrument in association with various imaging techniques.

Figure 3B:
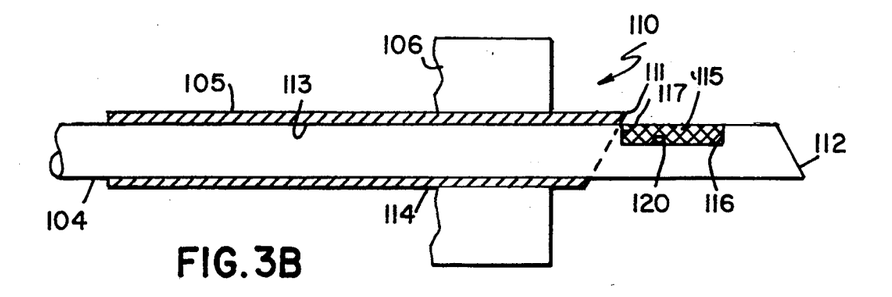
Figure 3C:
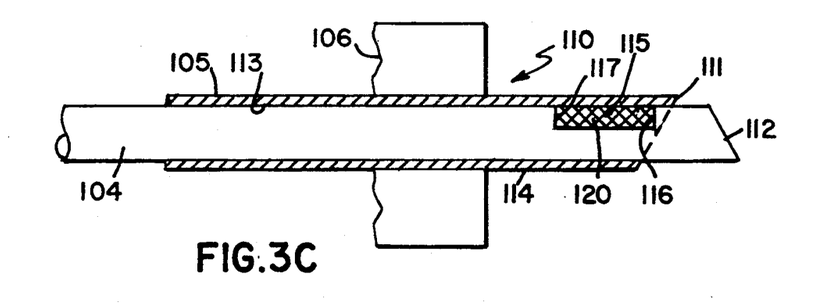

A notch 115 extends beyond the distal cutting edge 111 during operation to allow a portion of surrounding tissue to prolapse into the notch 115 between a distal radial end surface 116 and a proximal radial end surface 117. A flat base portion 120 extending between the distal and proximal end portions 116 and 117 supports the prolapsed tissue as shown in FIG. 3B. The cannula 105 then advances over the notch 115 to the position shown in FIG. 3C to sever the prolapsed tissue in the notch 115 from the adjacent tissue and to secure the sample.

In accordance with U.S. Pat. No. 5,195,533 a proximal end wall 121 may be formed proximally of the end wall 117 thereby to form an elongated notch 122 with an extended base 123 as shown by the dashed lines in FIG. 3A. This structure allows a single needle (i.e., a stylet 104 and cannula 105) to obtain multiple specimens and transport each successive specimen from the distal end of the notch to the proximal end thereby to store sequentially obtained specimens in axial sequence along the notch.

Referring again to FIGS. 1 and 2, a stylet slide operator 124 shown in FIG. 1 slides in slots 125 between a distal and a proximal position shown in FIG. 1. Similarly a cannula slide operator 126 moves in slots 127 between a distal position and a proximal position shown in FIG. 1. A selector switch 130 slides axially from the position shown from an unlocked position shown in FIG. 1 to a locked position. A firing button 131 triggers the system to enable the stylet 104 and the cannula 105 to displace distally in sequence.

In accordance with one aspect of this invention, the biopsy needle instrument 100 in FIGS. 1 and 2 obtains six specimens simultaneously. That is, when the physician moves the selector button 131, all the stylets 104 and cannulas 105 in six needles displace distally in sequence to collect six specimens simultaneously.

FIG. 2 discloses a stylet displacement structure 132 including a stylet carrier 133 that connects to the stylet slide operator 124 in FIG. 1 and to the proximal ends of each of the stylet means 104. The carrier 133 supports the stylets 104 for longitudinal movement in the control housing 101. Three of the stylet means 104a, 104b and 104c are shown in FIG. 2. When the stylet slide operator 124 in FIG. 1 moves to the proximal position, it displaces the stylet slide carrier 133 to the left beyond the position shown in FIG. 2 and compresses a stylet spring 134. When the stylet carrier 133 is fully retracted, a stylet latch 135 pivots on a pin 136. A pawl 137 engages the stylet carrier 133.

A cannula displacement structure 140 includes a cannula carrier 141 that connects to the cannula slide operator 126 in FIG. 1. When the cannula slide operator 126 moves to the proximal position, it retracts the cannula carrier 141 and compresses a cannula spring 142. When the cannula carrier 141 is fully retracted, a cannula latch 143 pivots about a pin 144 so a pawl 145 engages and latches the cannula carrier 141 in its retracted position. The latch 143 additionally includes an arm 147 proximate pin 144 that serves as a latch release. All the cannulas 105 connect to the cannula carrier 141. FIG. 2 particularly discloses a connection to cannulas 105a, 105b and 105c.

When both the stylet carrier 133 and cannula carrier 141 are latched in their retracted positions respectively, the physician can move the selector switch 130 to a proximal position (to the left in FIG. 2) thereby to slide an arm 147 and an end fitting 150 into a blocking position with respect to the latch 135. With the fitting 150 in this position, a force applied to the firing button 131 can not dislodge the latch 135. As disclosed in other embodiments, the selector switch 130 may also contain a distally extending arm and fitting for positively blocking the latch 143.

When the physician has positioned a distal end 151 of the sheath 106 at the selected tissue site, the selector switch 130 is moved to the distal position shown in FIG. 2. When the physician displaces the firing button 131, the latch 135 pivots on the pin 136 and releases the stylet carrier 133. The spring 134 displaces the carrier 133 and all the stylets 104 distally with a snap action. When the stylet carrier 133 reaches an extended position, it engages the arm 146 and rotates the latch 143 about the pin 144. The latch 143 then releases the cannula carrier 141 so the spring 142 advances the cannula carrier 141 and all the cannula 105 distally with a snap action thereby to complete the operation. When this operation is completed, each of the stylets 104 carriers a specimen. In this particular embodiment all the specimens have been obtained simultaneously.

Still referring to FIGS. 1 and 2, the sheath 106 performs several functions. Each needle comprises one stylet 104 and one cannula 105. Each is an elongated thin structure that is not particularly stable in a radial or transverse direction. Consequently, the needle also is not stable in a transverse direction. The sheath 106 contains axially extending internal passages that support the needles individually while permitting free reciprocal motion of the stylets 104 and cannula 105 along their respective axes. The sheath 106 also can reposition the stylets 104 and cannulas 105 and control the depth of the specimens in the tissue.

Figure 4:
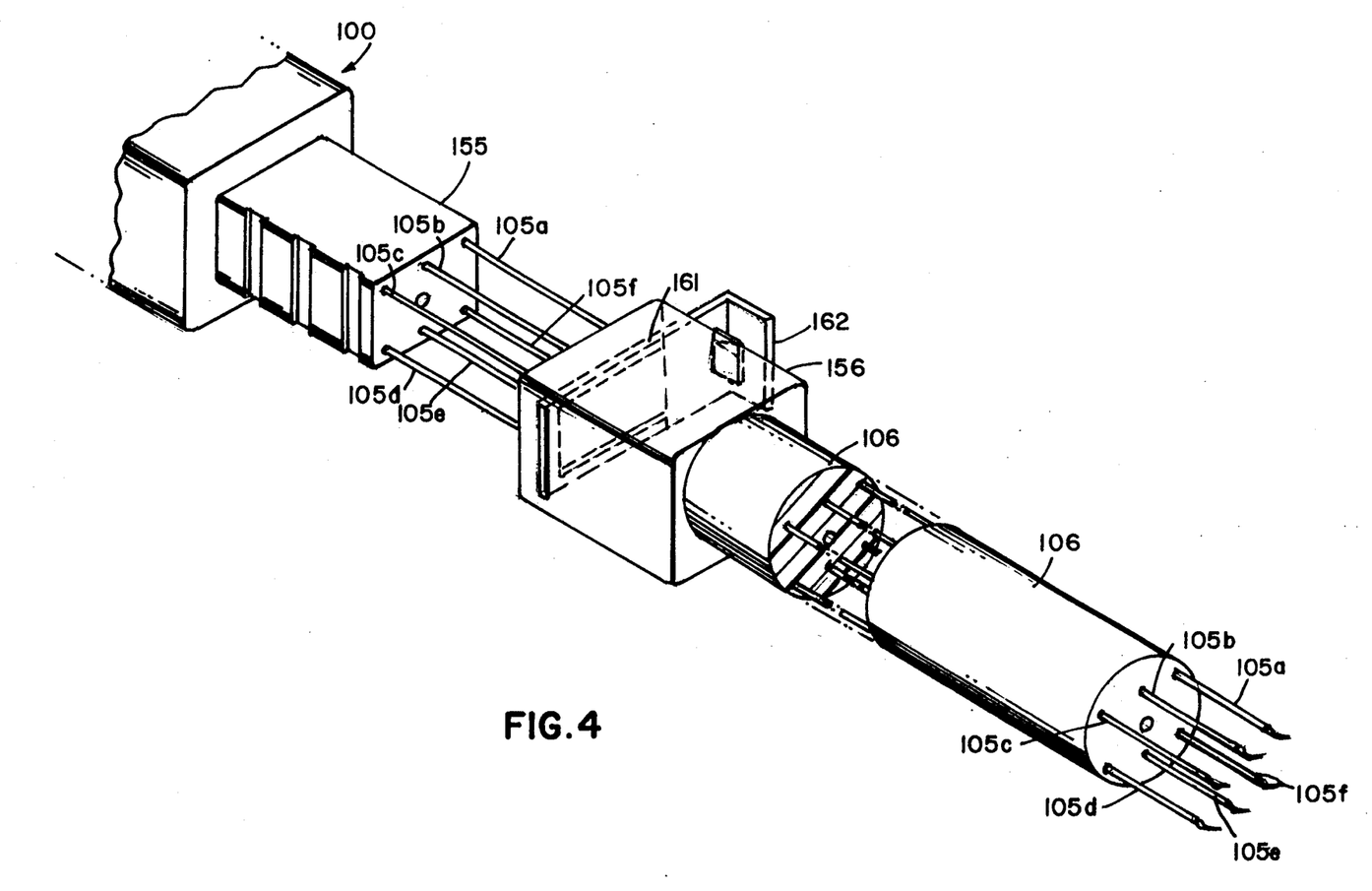
FIG. 4 is an enlarged perspective view of a portion of the instrument shown in FIG. 1.

As particularly shown in FIGS. 2 and 4, for example, the stylets 104 and the cannulas 105 exit the block 107 in a rectangular array of six needles. The sheath 106 repositions the needles in a transverse direction thereby to provide a circular needle array at the distal end 151 of the sheath 106. The relative lengths of the sheath 106 and the needles also can control the depth of each specimen.

Referring specifically to FIG. 4, six cannulas 105a through 105f extend from the block 107 in a rectangular array. A plurality of generally axially extending passages 152a through 152f carry each of the cannulas 105a through 105f respectively. These passages follow the paths necessary to displace the ends of the cannulas 105a through 105f and the contained stylets 104a through 104f in a transverse direction (i.e., essentially in the plane of the distal end 151) into a circular pattern. The displacement, if gradual, does not impact the freedom of relative axial motion between the cannulas 105 and the sheath 106 or between the cannulas 105 and the stylets 104. Although this particular embodiment shows the production of a circular array from a rectangular array, the passages in the sheath 106 may or may not change the position at all.

As previously indicated, the relative lengths of the sheath 106 and the stylets 104 and cannulas 105 can also be useful in controlling the specimen depth. In this application the distal end 151 can serve as a stop when it abuts tissue mass that is to be sampled. Consequently a shorter sheath 106 provides more stylet penetration. Conversely, a longer sheath 106 reduces stylet penetration.

Figure 5:
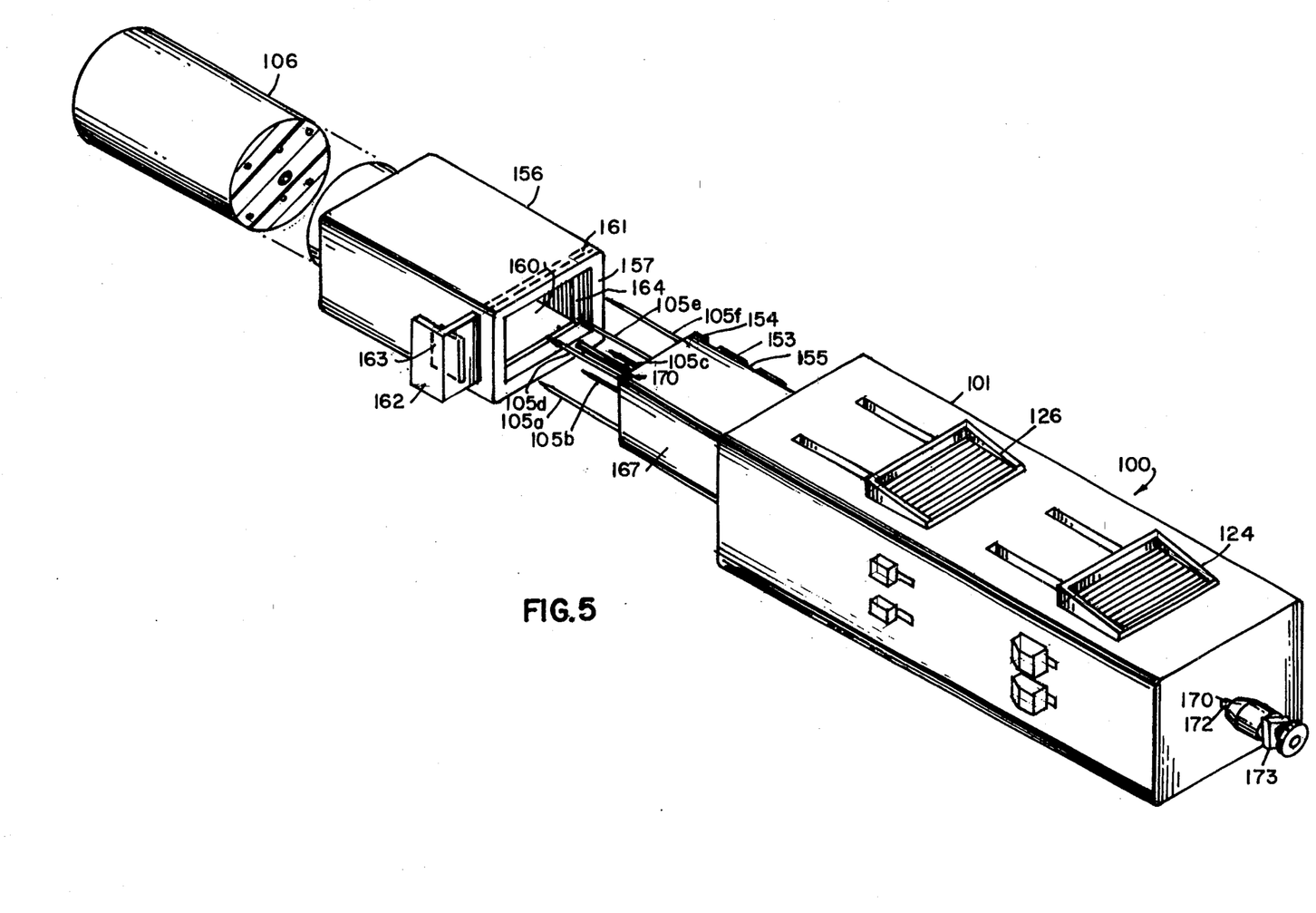
FIG. 5 is an enlarged perspective view of another portion of the instrument shown in FIG. 5.

FIG. 5 discloses a structure in which a single sheath 106 can be utilized to provide depth control. The block 107 on the distal end of the control housing 101 has a further adjustment block 153 extending axially from the block 107. One edge of the block 153 contains a plurality of rectangular, transverse spaced detents 155 formed therein.

A housing 156 that supports the sheath 106 has a structure at its proximal end 157 that forms an internal chamber 160 that slides over the adjustment block 153. An open rectangular slide structure 161 has a handle 162 and a biasing structure 163. The biasing structure 163 normally biases the slide 161 to the left as shown in FIG. 5 to expose a side member 164.

The physician compresses the operating handle 162 to displace the slide 164 to the right shown in FIG. 5 thereby opening the chamber 160 and allowing the chamber to slide over the adjustment block 153. When the position of the side member 164 and a detent 155 align, the biasing structure 163 moves the side member 164 into the detent. This, locks the housing 156 and the sheath 106 to the control housing 101. In this particular embodiment the physician can select one of three positions of the sheath 106 and consequently one of three specimen depths. Other detent structures could be substituted for that shown in FIG. 5 to provide coarser or finer axial position control and depth control.

In accordance with another feature of this invention, and as shown particularly with respect to FIGS. 1 and 5, the control housing 101 contains an aperture 170 that aligns axially with an aperture 171 through the sheath 106. These aligned apertures 170 and 171 constitute a passageway or channel for accepting auxiliary equipment. As particularly shown in FIG. 5, the auxiliary equipment includes a tube 172 that extends through the passages 170 and 171 to emerge at the distal end surface 151 of the sheath 106. This tube 172 may terminate at the proximal end with Luer-lock fitting 173 and can accommodate any of a variety of devices, such as optical devices or ultrasound transducers, for enabling a physician to monitor the biopsy site visually or otherwise.

Figure 6:
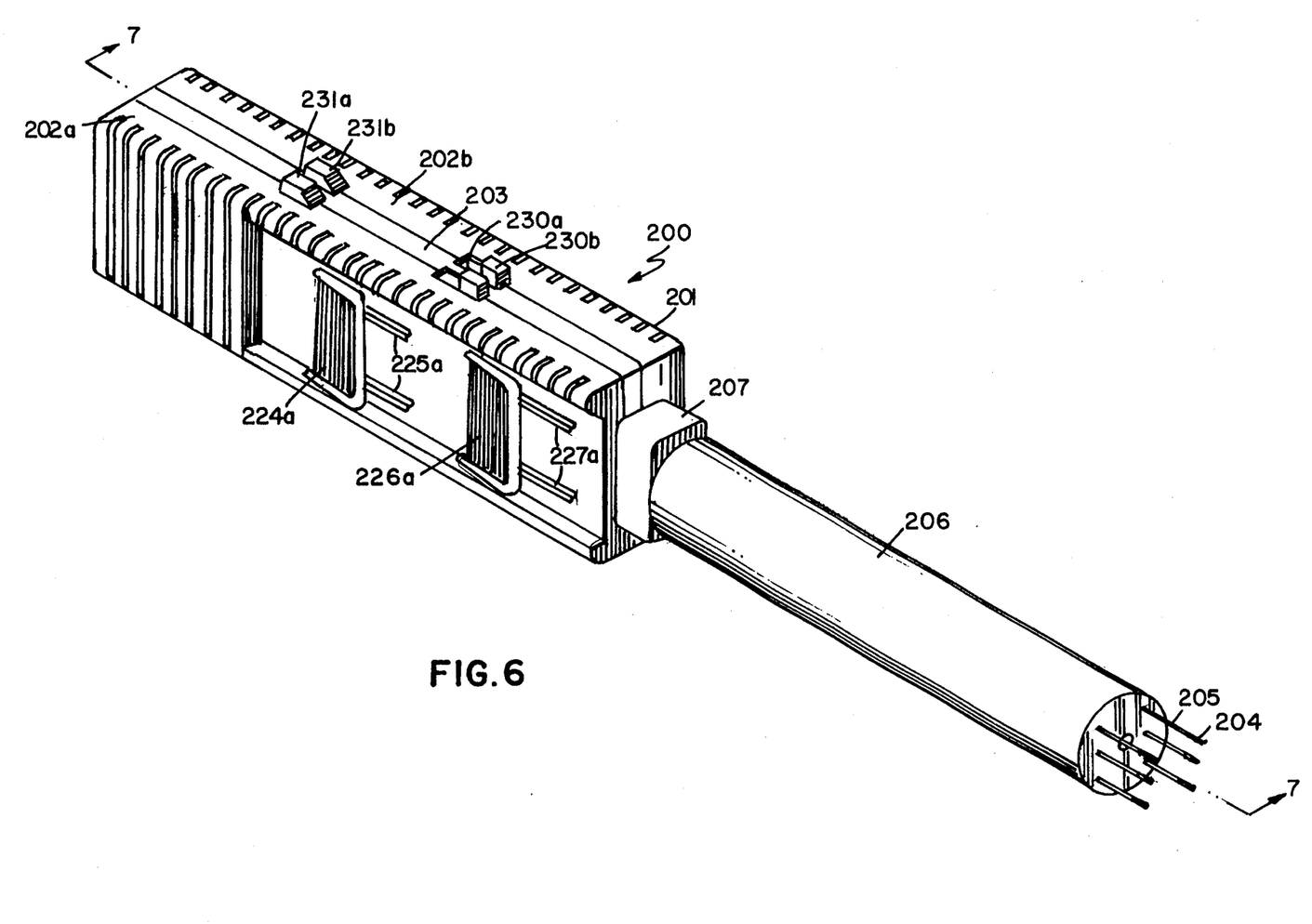
FIGS. 6 and 7 depict another embodiment of a biopsy needle instrument that incorporates this invention.
Figure 7:
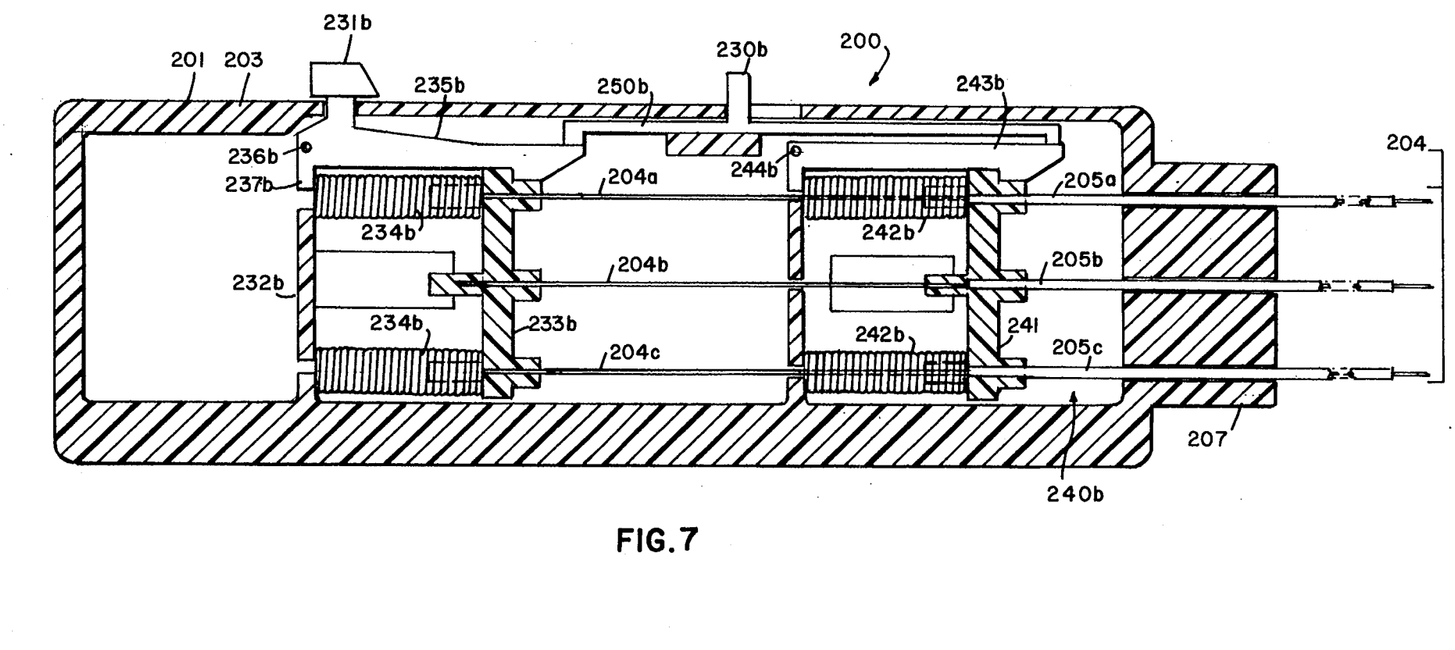

FIGS. 6 and 7 disclose an alternative embodiment of this invention in which a biopsy needle instrument 200 contains multiple stylets 204 and cannulas 205 grouped into a plurality of needle sets. A physician can control each needle set independently, so the physician can take multiple samples simultaneously in one or two successive sequences. This biopsy needle instrument 200 includes a control housing 201 that includes covers 202a and 202b and a base 203. The control housing 201 carries the various mechanisms for displacing the plurality of stylets 204 and cannulas 205 in the independent needle sets. A sheath 206 attaches to an end block 207 for performing the various functions corresponding to the sheath 106 in FIGS. 1 and 2.

In this particular embodiment, the control housing carries a first stylet slide operator 224a for retracting a first set of the stylets 204 by moving to the proximal position shown in FIGS. 6 along slots 225a. A slide operator 226a moves to the proximal position shown in FIG. 6 along slots 227a for retracting the corresponding cannula 205. A selector switch 230a and a firing button 231a operate in conjunction with the structure associated with the stylet slide operator 224a and cannula slide operator 226a.

The control housing 201 also contains another set of slide operators corresponding to slide operators 224a and 226a disposed in the cover 202b. A selector switch 230b and a firing button 231b control the operation of this apparatus that is shown more specifically in FIG. 7. The structure shown in FIG. 7 that is associated with the selector switch 230a and firing button 231b is independent of the structure associated with the selector switch 230a and firing button 231a.

More specifically, a stylet carrier 233b carries stylets 204a, 204b and 204c. When the corresponding stylet slide operator moves to its proximal position, it retracts the stylet carrier 233b and compresses springs 234b. As the springs 234b are compressed, one of the springs 234b biases a latch 235b into a latched position by applying a latching force about a pin 236b as it bears against an arm 237b. Similarly, a cannula carrier 241b carries cannulas 205a, 205b and 205c. A corresponding cannula slide operator retracts the carrier 241b, compressing cannula springs 243b and setting a latch 243b that pivots about a pin 244b. The selector switch 230b includes oppositely extending arms 248b and 250b. With the arms in the position shown in FIG. 7, they block any motion of the latches 243b and 235b respectively. When the selector switch 230b is moved to a distal position (to the right in FIG. 7), subsequent displacement of the firing button 231b pivots the latch 235b and allows the springs 234b to displace the stylet carrier 233b distally with a snap action. When the stylet carrier 233b extends fully, it strikes an arm 245b causing the latch 243b to pivot and free the cannula carrier 241b. The springs 242b then drive that carrier 241b and the attached cannulas 105a through 105c to the right with a snap action.

As will thus be apparent from FIGS. 6 and 7, a physician can selectively obtain three specimens by displacing the firing button 231a and three additional specimens by operating the fire button 231b independently of each other.

Figure 8:
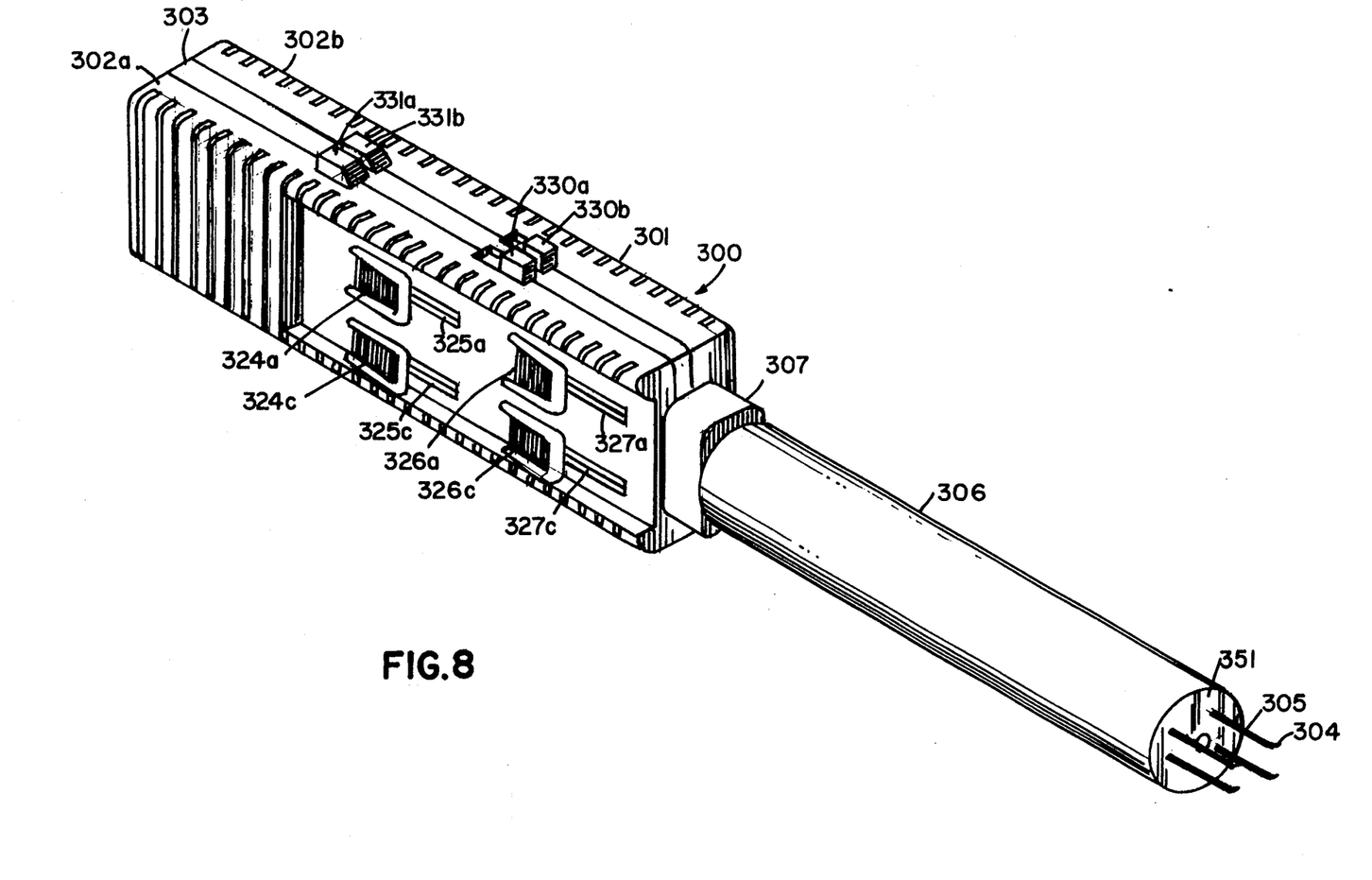
FIGS. 8 and 9 depict still another embodiment of a biopsy needle instrument that incorporates this invention.
Figure 9:
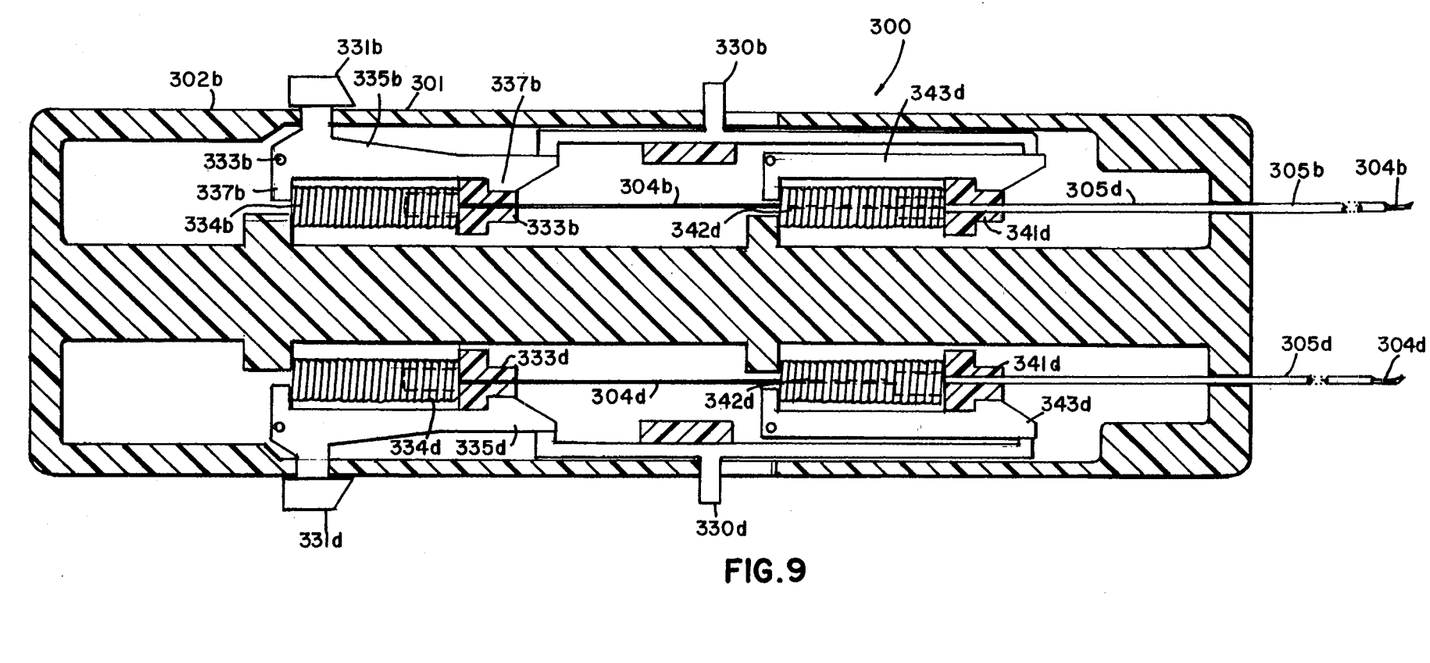

FIGS. 8 and 9 depict another embodiment of a biopsy needle instrument 300 comprising a control housing 301 with side covers 302a and 302b and a central housing 303. In this particular embodiment the control housing 301 supports four needles including stylets 304 and cannula 305 that can be fired independently with respect to each other. More particularly, the cover 302a carries a stylet slide operator 324a and a stylet operator 324c that slide independently in slots 325a and 325c. Similarly the cover 302a carries cannula slide operators 326a and 326c that ride in slots 327a and 327c. Corresponding slide operators are positioned on the face of the cover 302b.

A sheath 306 supports the stylets 304 and cannulas 305 and attaches to an end block 307. A selector switch 330a and a firing button 331a control the operation of the stylet 304a and cannula 305a. As more clearly shown in FIG. 9, a selector switch 330b and a firing button 331b control the operation of the stylet 304b and cannula 305b. As the covers 302a and 302b are similar, FIG. 9 depicts only the components with respect to the cover 302b.

In this particular embodiment, each of the stylets 304b and 304d connects to independent stylet carriers 333b and 333d respectively. Each can be retracted independently by stylet slide operators mounted in the cover 203b corresponding to the stylet slide operators 324a and 324c. As each slide operator is retracted, it retracts the corresponding one of the stylet carriers 333b and 333d compressing corresponding springs 334b and 334d. Referring particularly to the mechanism associated with the stylet 304b, the spring 334b biases a latch 335b about a pin 336b by engaging an arm 337b. When the corresponding slide operator fully retracts the carrier 333b, an arm 337b latches the stylet carrier 333b. Similarly, the operation of slide operator associated with a stylet 304d retracts the carrier 333d compressing a spring 334d and eventually causing a latch 335d to capture the carrier 333d in its retracted position.

A cannula carrier 341b attaches to cannula 305b. When the Cannula carrier 341b is retracted, it compresses the spring 342b and, when fully retracted, the latch 343d captures and retains the cannula carrier 341b in the retracted position. Similarly, a cannula carrier 341d carries the cannula 305d. As it moves to a retracted position, it compresses a spring 342d and, when fully retracted, a latch 343d captures the cannula carrier 341d. Selector switches 330b and 330d can move between blocking and nonblocking positions thereby to enable latch motion independently for each needle assembly.

In this particular embodiment, the movement of a particular selector switch, such as selector switch 330b, to a proximal position and the displacement of a corresponding firing button, such as firing button 331b, causes the springs 334b and 342b to displace the stylet carrier 333b and the cannula carrier 335b distally in sequence thereby to capture a sample at the distal end of the stylet 304b where they emerge from a distal end 351 of the sheath 306. In this particular embodiment, therefore, it will be apparent that the control housing 301 contains four independent controls that enable a physician to selectively take a single sample with each of the stylets 304a through 304d in sequence in a predetermined pattern without repositioning or relocation.

Therefore, in accordance with the various objects of this invention, there have been disclosed diverse biopsy needle instruments and methods for capturing multiple tissue specimens. In each case multiple specimens can be obtained without any requirement for repositioning or relocation of the instrument. The use of multiple needles and a supporting sheath 106 enables a physician to establish a predetermined pattern of specimen sites. Changing the effective length of the sheath control the depth of any biopsy. Consequently the physician can use this instrument and method to obtain multiple specimens in a precise, predetermined three dimensional pattern of tissue sites. This instrument and method can be used in a variety of environments, are easy to use and can be used efficiently.

This invention has been described in terms of specific structures. It will be apparent, however, that a number of variations and modifications can be made to these specifically disclosed structures. For example, a given of a biopsy needle instrument may comprise the disclosed four or six single needles or other numbers of needles. The auxiliary channel disclosed in FIGS. 1 and 5 may be omitted. The location of the various controls such as the selector switch, firing buttons and slide operators can be altered as can be the specific structure for retracting or displacing distally each of the cannulas and stylets. Each needle assembly may be configured to take one sample or multiple samples. Therefore, it is the intent of the appended claims to cover all such variations and modifications as come within the true spirit and scope of this invention.

What is claimed as new and desired to be secured by Letters Patent of the United States is:

1. A biopsy needle instrument for taking multiple specimens from surrounding tissue in a predetermined pattern comprising:

A. a housing,

B. a plurality of axially elongated stylet means extending between proximal positions at said housing and distal positions along an axis thereby to define a plurality of specimen positions according to the predetermined pattern, C. a plurality of cannula means for severing specimens from surrounding tissue, each said cannula means extending from said housing along the axis and being disposed about a corresponding one of said stylet means, D. stylet displacement means for reciprocating said plurality of stylet means relative to said plurality of cannula means and to said housing and parallel to the axis between extended and retracted axial positions, E. cannula displacement means for reciprocating said plurality of cannula means relative to said stylet means and to said housing and parallel to the axis between extended and retracted axial positions, whereby said biopsy needle instrument obtains multiple specimens from the tissue in the predetermined pattern by sequential operation of said stylet displacement means and said cannula displacement means, and F. support means for supporting said plurality of cannula means in the predetermined pattern.

2. A biopsy needle instrument as recited in claim 1 wherein said support means includes elongated sheath means for supporting said plurality of stylet and cannula means in the predetermined pattern.

3. A biopsy needle instrument as recited in claim 2 wherein said support means includes independent guide passages for each of said stylet and cannula means that reposition the distal positions thereof with respect to the proximal positions thereby to produce the predetermined pattern.

4. A biopsy needle instrument as recited in claim 2 additionally including adjustable means connected to said support means and said housing means for adjusting the position of said support means with respect to the distal ends of said stylet and cannula means.

5. A biopsy needle instrument as recited in claim 2 wherein said housing and said support means have aligned central passages therethrough parallel to said stylet and cannula means for accommodating an ancillary structure.

6. A biopsy needle instrument as recited in claim 1 wherein each said stylet means comprises a side-opening notch formed adjacent the distal end thereof for capturing a specimen of predetermined length.

7. A biopsy needle instrument as recited in claim 6 wherein said side-opening notch has an axial length along said stylet means that is greater that the predetermined specimen length.

8. A biopsy needle instrument as recited in claim 1 wherein said stylet displacement means and said cannula displacement means include stylet carrier means for connecting each of said stylet means for simultaneous displacement, cannula carrier means for connecting each of said cannula means for simultaneous displacement and means for displacing said stylet carrier means and said cannula carrier means distally in sequence whereby said biopsy needle instrument obtains multiple specimens from the tissue in the predetermined pattern simultaneously.

9. A biopsy needle instrument as recited in claim 1 wherein said stylet displacement means and said cannula displacement means include at least first and second stylet carrier means for connecting certain of said stylet means into discrete sets for simultaneous displacement, cannula carrier means for connecting corresponding ones of each of said cannula means into discrete sets for simultaneous displacement, and independent means for displacing each of said stylet carrier means and said cannula carrier means distally in sequence whereby said biopsy needle instrument obtains multiple specimens from the tissue in the predetermined pattern in a series of discrete operations that each obtain a plurality of specimens.

10. A biopsy needle instrument as recited in claim 1 wherein said stylet displacement means and said cannula displacement means include a plurality of stylet carrier means for independent connection to a said stylet means, a plurality of cannula carrier means for independent connection to a said cannula means and independent means for displacing each of said stylet carrier means and said cannula displacement means distally in sequence whereby said biopsy needle instrument obtains multiple specimens from the tissue in the predetermined pattern in a series of discrete operations that each obtain a single specimen.

11. A biopsy needle instrument for taking multiple specimens from surrounding tissue in a predetermined pattern comprising:

A. a housing,

B. a plurality of axially elongated stylet means extending between proximal positions at said housing and distal positions along an axis thereby to define a plurality of specimen positions according to the predetermined pattern, C. a plurality of cannula means for severing specimens from surrounding tissue, each said cannula means extending from said housing along the axis and being disposed about a corresponding one of said stylet means, D. stylet displacement means and cannula displacement means for moving along the axis said plurality of stylet means and said plurality of cannula means respectively and independently relative to each other and to said housing between extended and retracted positions, each of said stylet means and each of said cannula means being connected to said stylet displacement means and to said cannula displacement means respectively whereupon simultaneous extension of said plurality of stylet means by said stylet displacement means defines the plurality of the specimen positions and simultaneous extension of said plurality of cannula means by said cannula displacement means severs the specimens from the defined positions whereby said biopsy needle instrument obtains all the specimens from the tissue in the predetermined pattern simultaneously; and E. support means for supporting said cannula means in the predetermined pattern.

12. A biopsy needle instrument as recited in claim 11 wherein each of said stylet displacement means and said cannula displacement means includes latching means for retaining said stylet displacement means and said cannula displacement means in a retracted position and means for enabling said stylet displacement means to simultaneously displace said plurality of said stylet means distally and said cannula displacement means to simultaneously displace said plurality of said cannula means distally.

13. A biopsy needle instrument as recited in claim 12 wherein said stylet displacement means includes:

i. a stylet carrier supported for longitudinal movement in said housing and connected to the proximal ends of each of said stylet means,
ii. stylet retracting means connected to said stylet carrier means for retracting said stylet carrier means,
iii. stylet spring means connected between said stylet carrier means and said housing for being compressed when said stylet means is retracted,
iv. stylet latch means engaging said stylet carrier means for retaining said stylet carrier means in said retracted position, and
v. release means for displacing said stylet latch means to allow said stylet spring means to displace said stylet means distally.

14. A biopsy needle instrument as recited in claim 13 wherein said cannula displacement means includes:
i. a cannula carrier supported for longitudinal movement in said housing and connected to the proximal ends of each of said cannula means,
ii. cannula retracting means connected to said cannula carrier means for retracting said cannula carrier means,
iii. cannula spring means connected between said cannula carrier means and said housing for being compressed when said cannula means is retracted, and
iv. cannula latch means engaging said cannula carrier means for retaining said cannula carrier means in said retracted position, said stylet carrier means release means displacing said cannula latch means to allow said cannula spring means to displace said cannula means distally.

15. A biopsy needle instrument as recited in claim 14 wherein said stylet displacement means and cannula displacement means additionally comprise locking means mounted for longitudinal displacement in said housing and including operating means for moving said locking means between first and second positions and means connected to said operating means for blocking and permitting movement of said stylet and cannula latch means when said operating means is in the first and second positions respectively.

16. A biopsy needle instrument as recited in claim 15 wherein said support means includes elongated sheath means for supporting said plurality of stylet and cannula means in a predetermined pattern.

17. A biopsy needle instrument as recited in claim 16 wherein said sheath means includes independent passages for each of said stylet and cannula means that reposition the location of the distal positions thereof with respect to the proximal positions thereby to alter the pattern of the biopsies.

18. A biopsy needle instrument as recited in claim 16 additionally including adjustable means connected to said sheath means and said housing means for adjusting the position of said sheath means with respect to the distal ends of said stylet and cannula means.

19. A biopsy needle instrument as recited in claim 16 wherein said housing and said sheath means have aligned central passages therethrough parallel to said stylet and cannula means for accommodating an auxiliary structure.

20. A biopsy needle instrument as recited in claim 16 wherein each said stylet means comprises a side-opening notch formed adjacent the distal end thereof for capturing specimens of a predetermined length, said side-opening notch having an axial length that is greater that the predetermined specimen length.

21. A biopsy needle instrument for taking multiple specimens from surrounding tissue in a predetermined pattern comprising:
A. a housing,
B. first and second sets of axially elongated stylet means extending between proximal positions at said housing and distal positions thereby to define a plurality of specimen positions according to the predetermined pattern,
C. first and second sets of cannula means for severing specimens from surrounding tissue, each said cannula means extending from said housing and being disposed about a corresponding one of said stylet means, and
D. first and second displacement means for displacing distally said stylet and cannula means in a corresponding set in sequence and independently whereby said biopsy needle instrument obtains the specimens from the tissue in the predetermined pattern, all the specimens in a given set obtained simultaneously.

22. A biopsy needle instrument as recited in claim 21 wherein each of said first and second displacement means includes stylet displacement means for extending and retracting said corresponding set of stylet means simultaneously, cannula displacement means for extending and retracting said corresponding set of cannula means simultaneously, latching means for retaining said stylet and cannula displacement means in a retracted position and means for enabling said stylet and cannula displacement means to displace said plurality of stylet means and said plurality of cannula means distally and sequentially whereby said first and second sets of stylet and cannula means operate independently.

23. A biopsy needle instrument as recited in claim 22 wherein each said stylet displacement means includes:
i. a stylet carrier supported for longitudinal movement in said housing and connected to the proximal ends of each of said stylet means in a corresponding set,
ii. stylet retracting means connected to said stylet carrier means for retracting said stylet carrier means,
iii. stylet spring means connected between said stylet carrier means and said housing for being compressed when said stylet means is retracted,
iv. stylet latch means engaging said stylet carrier means for retaining said stylet carrier means in said retracted position, and
v. release means for displacing said stylet latch means to allow said stylet spring means to displace said stylet means distally.

24. A biopsy needle instrument as recited in claim 23 wherein said cannula displacement means includes:
i. a cannula carrier supported for longitudinal movement in said housing and connected to the proximal ends of each of said cannula means in a corresponding set,
ii. cannula retracting means connected to said cannula carrier means for retracting said cannula carrier means,
iii. cannula spring means connected between said cannula carrier means and said housing for being compressed when said cannula means is retracted, and iv. cannula latch means engaging said cannula carrier means for retaining said cannula carrier means in said retracted position, said stylet carrier means release means displacing said cannula latch means to allow said cannula spring means to displace said cannula means distally.

25. A biopsy needle instrument as recited in claim 24 wherein said stylet displacement means and cannula displacement means additionally comprise locking means mounted for longitudinal displacement in said housing and including operating means for moving said locking means between first and second positions and means connected to said operating means for blocking and permitting movement of said corresponding stylet and cannula latch means when said operating means is in the first and second positions respectively.

26. A biopsy needle instrument as recited in claim 25 additionally comprising elongated sheath means for supporting said plurality of stylet and cannula means in a predetermined pattern.

27. A biopsy needle instrument as recited in claim 26 wherein said sheath means includes independent passages for each of said stylet and cannula means that reposition the location of the distal positions thereof with respect to the proximal positions thereby to alter the pattern of the biopsies.

28. A biopsy needle instrument as recited in claim 26 additionally including adjustable means connected to said sheath means and said housing means for adjusting the position of said sheath means with respect to the distal ends of said stylet and cannula means.

29. A biopsy needle instrument as recited in claim 26 wherein said housing and said sheath means have aligned central passages therethrough parallel to said stylet and cannula means to accommodate an auxiliary structure.

30. A biopsy needle instrument as recited in claim 26 wherein each said stylet means comprises a side-opening notch formed adjacent the distal end thereof for capturing specimens of a predetermined length, said side-opening notch having an axial length that is greater that the predetermined specimen length.

31. A biopsy needle instrument for taking multiple specimens from surrounding tissue in a predetermined pattern comprising:
A. a housing,
B. a plurality of axially elongated stylet means extending between proximal positions at said housing and distal positions thereby to define a plurality of specimen positions according to the predetermined pattern,
C. a plurality of cannula means for severing specimens from surrounding tissue, each said cannula means extending from said housing and being disposed about a corresponding one of said stylet means, and
D. independent displacement means for displacing distally each said stylet means and cannula means whereby said biopsy needle instrument obtains the multiple specimens from the tissue in the predetermined pattern, each specimen being obtained individually.

32. A biopsy needle instrument as recited in claim 31 wherein each said independent displacement means includes stylet displacement means for extending and retracting a corresponding stylet means, cannula displacement means for extending and retracting a corresponding cannula means, latching means for retaining said stylet and cannula displacement means in a retracted position and means for enabling said stylet and cannula displacement means to displace the corresponding stylet means and cannula means displace sequentially.

33. A biopsy needle instrument as recited in claim 32 wherein each said stylet displacement means includes:
i. a stylet carrier supported for longitudinal movement in said housing and connected to the proximal end of a corresponding stylet means,
ii. stylet retracting means connected to said stylet carrier means for retracting said stylet carrier means,
iii. stylet spring means connected between said stylet carrier means and said housing for being compressed when said stylet means is retracted,
iv. stylet latch means engaging said stylet carrier means for retaining said stylet carrier means in said retracted position, and
v. release means for displacing said stylet latch means to allow said stylet spring means to displace said stylet means distally.

34. A biopsy needle instrument as recited in claim 33 wherein said cannula displacement means includes:
i. a cannula carrier supported for longitudinal movement in said housing and connected to the proximal end of a corresponding cannula means,
ii. cannula retracting means connected to said cannula carrier means for retracting said cannula carrier means,
iii. cannula spring means connected between said cannula carrier means and said housing for being compressed when said cannula means is retracted, and
iv. cannula latch means engaging said cannula carrier means for retaining said cannula carrier means in said retracted position, said corresponding stylet carrier means release means displacing said cannula latch means to allow said cannula spring means to displace said cannula means distally.

35. A biopsy needle instrument as recited in claim 34 wherein each said independent displacement means additionally comprises locking means mounted for longitudinal displacement in said housing and including operating means for moving said locking means between first and second positions and means connected to said operating means for blocking and permitting movement of said corresponding stylet and cannula latch means when said operating means is in the first and second positions respectively.

36. A biopsy needle instrument as recited in claim 35 additionally comprising elongated sheath means for supporting said plurality of stylet and cannula means in a predetermined pattern.

37. A biopsy needle instrument as recited in claim 36 wherein said sheath means includes independent passages for each of said stylet and cannula means that reposition the location of the distal positions thereof with respect to the proximal positions thereby to alter the pattern of the biopsies.

38. A biopsy needle instrument as recited in claim 36 additionally including adjustable means connected to said sheath means and said housing means for adjusting the position of said sheath means with respect to the distal ends of said stylet and cannula means.

39. A biopsy needle instrument as recited in claim 36 wherein said housing and said sheath means have aligned central passages therethrough parallel to said stylet and cannula means for accommodating an auxiliary structure.

40. A biopsy needle instrument as recited in claim 36 wherein each said stylet means comprises a side-opening notch formed adjacent the distal end thereof for capturing specimens of a predetermined length, said side-opening notch having an axial length that is greater that the predetermined specimen length.

41. A method for taking multiple biopsies from a tissue mass in a predetermined pattern using a biopsy instrument comprising:
A. grouping a plurality of axially rigid, transversely flexible elongated stylets and coaxial cannulas in the instrument along essentially parallel axes from proximal to distal ends thereof whereby said distal ends are arrayed in the predetermined pattern and whereby the stylets and cannulas are adapted for motion relative to each other along the axes,
B. positioning the grouped stylets and cannulas proximate the tissue mass,
C. transversely stabilizing the stylets and cannulas thereby to assure that the distal ends remain in the predetermined pattern, and
D. displacing simultaneously at least two of the stylets distally along the axes into the tissue and thereafter displacing simultaneously the corresponding cannulas distally along the axes to capture at least two specimens, the simultaneous displacement of all the stylets and subsequent displacement of all the cannulas while the instrument is located at one position thereby capturing plural specimens from the positions of the predetermined pattern.

42. A method for taking multiple biopsies as recited in claim 41 wherein said stabilizing step includes the positioning of a sheath over a predetermined portion of the stylets and cannulas to individually support each cannula in a transverse plane, said method additionally including the step of adjusting the axial position of the sheath thereby to control the depth of each specimen.

43. A method for taking multiple biopsies as recited in claim 41 wherein said stabilizing step includes the positioning of a sheath over a predetermined portion of the stylets and cannulas to individually support each cannula in a transverse plane and to reorient the pattern of the stylets and cannulas between the proximal and distal ends.

44. A method for taking multiple biopsies from a tissue mass in a predetermined pattern using a biopsy instrument comprising:
A. grouping a plurality of elongated stylets and coaxial cannulas in the instrument along essentially parallel axes from proximal to distal ends thereof to define a plurality of sets of corresponding stylets and cannulas such that each set includes at least one corresponding stylet and cannula whereby said distal ends are arrayed in the predetermined pattern and whereby the plurality of the stylets and the plurality of the cannulas are adapted for motion relative to each other along the axes,
B. positioning the sets of the plurality of stylets and cannulas proximate the tissue mass,
C. displacing one set of the corresponding stylets and cannulas distally along the axes into the tissue independently of the other of the sets of the corresponding stylets and cannulas to thereby captures speci4mens according to the arrangement of the one set, and
D. displacing the other of the sets of the corresponding the stylets and cannulas independently of the one set whereby displacement of all of the sets with the instrument in the position proximate the tissue mass thereby captures plural specimens from the positions of the predetermined pattern.

45. A method for taking multiple biopsies as recited in claim 44 wherein at least one of said first and second displacement steps distally displaces a single stylet and cannula.

46. A method for taking multiple biopsies as recited in claim 44 wherein said method includes the additional step of simultaneously monitoring the biopsy site.

* * * * *